United States Patent
Bartels et al.

(10) Patent No.: US 7,613,498 B2
(45) Date of Patent: Nov. 3, 2009

(54) DEVICE FOR SUPPORTING A PATIENT FOR COMPUTER TOMOGRAPHS

(75) Inventors: Frank Bartels, Seybothenreuth (DE); Peter Knappe, Bamberg (DE); Stefan Leidenberger, Schriesheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/577,593

(22) PCT Filed: Oct. 27, 2004

(86) PCT No.: PCT/EP2004/052678

§ 371 (c)(1),
(2), (4) Date: Apr. 26, 2006

(87) PCT Pub. No.: WO2005/041776

PCT Pub. Date: May 12, 2005

(65) Prior Publication Data

US 2007/0094796 A1 May 3, 2007

(30) Foreign Application Priority Data

Oct. 31, 2003 (DE) ................. 103 50 901

(51) Int. Cl.
*A61B 5/05* (2006.01)
*A47B 13/00* (2006.01)
*H05G 1/02* (2006.01)
(52) U.S. Cl. ................... 600/425; 5/601; 378/196
(58) Field of Classification Search ............... 600/425; 378/196; 5/601
See application file for complete search history.

(56) References Cited

U.S. PATENT DOCUMENTS

| 4,360,936 A | 11/1982 | Keller |
| 5,014,292 A * | 5/1991 | Siczek et al. ............ 378/196 |
| 5,410,584 A * | 4/1995 | Schaefer et al. .......... 378/196 |
| 5,525,905 A * | 6/1996 | Mohapatra et al. ........ 324/318 |
| 6,195,578 B1 | 2/2001 | Distler et al. |
| 6,637,056 B1 | 10/2003 | Tybinkowski et al. |
| 2002/0112288 A1 | 8/2002 | Seufert |

FOREIGN PATENT DOCUMENTS

| CN | 1171229 | 1/1998 |
| DE | 101 08 549 | 3/2002 |
| EP | 0 812 567 A1 | 12/1997 |
| FR | 2 529 088 | 12/1983 |
| GB | 2 286 887 A | 8/1995 |

OTHER PUBLICATIONS

Chinese Office Action dated Apr. 10, 2008 for 200480032179.3 with English translation.

* cited by examiner

*Primary Examiner*—Eric F Winakur
*Assistant Examiner*—Michael T Rozanski
(74) *Attorney, Agent, or Firm*—Brinks, Hofer, Gilson & Lione

(57) ABSTRACT

A device for supporting a patient is used with a computer-tomography (CT) device. The patient to be examined is to be introduced into an opening in a gantry of the CT device. The patient supporting device has a height-adjustable device disposed laterally with respect to the gantry opening and permits the height of a support for a patient to be adjusted. A support arm extends from the height-adjustable device to a fixture for supporting a stretcher and is rotatable with respect to the height adjustable device.

14 Claims, 2 Drawing Sheets

DEVICE FOR SUPPORTING A PATIENT FOR COMPUTER TOMOGRAPHS

TECHNICAL FIELD

This application relates to a device for supporting a patient for a computer tomography device, and to a computer tomograph having such a device for supporting a patient.

BACKGROUND

Computer tomography devices (CTs), serve to make three-dimensional images or images of slices through a body to be examined. The image data are obtained by means of X-radiation, using an X-ray beam source that rotates on a circular path around the body to be examined. An X-ray detector rotates jointly with the X-ray beam source, but diametrically opposite to the beam source, and detects the raw image data.

The raw image data represent two-dimensional X-ray projections with many different projection directions, corresponding to the rotation. From the two-dimensional X-ray projections, slice images or three-dimensional X-ray images are generated by a computer.

The quality of the X-ray images that can be generated depends substantially on the stable, exact position of the body to be examined. Deviations in the position of the body from the optimal position in the CT and changes in the body position during the time-consuming acquisition of the X-ray image data impair the quality of the resultant images.

To be able to assure the stable and exact positioning of the body of the patient in the CT, a device for supporting a patient is provided. A CT has a so-called "gantry", inside of which the X-ray beam source and the X-ray image detector rotate. At the center of rotary motion, the gantry has an opening, in which the patient is positioned for the acquisition of the raw image data. The device for supporting a patient serves to slide a patient, supported on the supporting device, into the opening in the gantry.

The supporting device is sufficiently stable to be able to bear the weight of the patient, and sufficiently movable to enable positioning the patient inside the gantry.

However, sagging of the device for supporting a patient or of a stretcher placed on the supporting device from the weight of the patient cannot be avoided. Such sagging may be reduced by means of additional structural provisions, such as additional braces.

The device for supporting a patient is intended to allow placing the patient or the stretcher along with the patient onto it without problems. To that end, the supporting device should be movable in many directions and in particular should be capable of being lowered quite far, so that a patient being placed on it or shifted to the supporting device need not be lifted. On the one hand, this puts less of a burden on the medical staff. On the other, this also is beneficial to the patient, for whom, depending on physical condition, the shifting can be unpleasant and painful. Especially when a patient is being examined by more than one kind of medical equipment, such as a CT as well as a C-arch X-ray machine, the frequent shifting from one machine to another is a great burden and entails great effort.

German Patent Disclosure DE 101 08 549, teaches supporting a patient on a stretcher that can be moved by a so-called trolley, or movable carriage. To make a CT scan, the stretcher is placed on a fixed base, located in front of the gantry of a CT, with which the stretcher can be introduced into the gantry and removed again. The fixed base assures stable positioning of the patient, but does not offer any further motion capabilities.

SUMMARY

A device for supporting a patient for a CT which assures stable positioning of the patient with respect to a CT or other device and at the same time offers versatile movability is disclosed. A CT with a device for supporting a patient is provided in which stable positioning of the patient and at the same time versatile movability are assured.

A device supports a patient for a computer tomography device and a computer tomography device having such a device for supporting a patient includes a gantry with an examination opening for introducing a patient to be examined. The device for supporting a patient has a height adjuster, for supporting a stretcher adjustably in height. The height adjuster may be mounted on a computer tomography device in such a way that it is located laterally with respect to the examination opening. An effect of the lateral location of the height adjuster is that the space underneath the examination opening in front of the gantry remains free, and a patient or a stretcher can be lowered especially far when disposed in that position. The lowerability is not hindered by the location of the height adjuster. An optimal height in a given instance can be selected for placing a patient on a stretcher or shifting the patient. Support of the patient or the stretcher in the immediate vicinity in front of the examination opening may also be provided, resulting in stable support of the patient and reducing sagging of the stretcher from the patient's weight.

In an aspect, the height adjuster can be mounted on the computer tomography (CT) device in such a way that it is located laterally with respect to the gantry. In such a position, the height adjuster does not impede a tilting motion of the gantry about a horizontal axis, and such a motion being useful in the field of medical diagnosis. The gantry can be tilted unhindered next to and thus past the height adjuster.

In another aspect, the height adjuster has a load-bearing arm disposed to support the stretcher. The load-bearing arm is connected to the height adjuster such that the height thereof is adjustable by the height adjuster. The load-bearing arm is supported rotatably about a vertical axis. With the patient lying on the stretcher, the load bearing arm can be pivoted out of the way of the gantry. This additional movability may facilitate the positioning of the device for supporting a patient, for placing the patient on the device, or for shifting the patient onto the device. A patient lying on the device may be swiveled either toward the gantry or toward some other kind of medical equipment, such as a C-arch X-ray machine. By moving the patient to the other device using the device for supporting a patient, another medical examination is made possible without first shifting the patient to another stretcher. This reduces the burden both on the medical staff and on the patient.

In yet another aspect, the device for supporting a patient has a rotary bearing which is mounted on the load-bearing arm and supports the stretcher rotatably about a vertical axis. The rotary bearing represents a second axis of rotation, which expands the motion capabilities of the device for supporting a patient. In addition to permitting motion of the stretcher toward the gantry or away from the gantry, the stretcher may be rotated in any pivoted position. The additional rotatability can also be used to reduce the space required for pivoting motions, and the pivoting radius of the device for supporting a patient together is reduced.

In still another aspect, the device for supporting a patient has a stretcher guide, which is mounted on a rotary bearing rotatable about a vertical axis and is configured to support a stretcher longitudinally displaceably. The stretcher, with the patient lying on it, may be slid into the gantry or back out again, representing a further possibility for flexible positioning of the patient or the stretcher.

In a further aspect, the device for supporting a patient has a second height adjuster for supporting a stretcher adjustably in height and which can be mounted on the computer tomography device in such a way that the second height adjuster is located laterally with respect the examination opening. The patient may be supported by either one or the other of the height adjusters. Two stretchers can, for instance, be slid into or out of the gantry in alternation. The alternating use makes more efficient use of a computer tomography device possible, as one patient may be prepared using the one height adjuster, while another patient may be examined in the computer tomography device, using the other height adjuster.

In a still further aspect, the second height adjuster supports a stretcher on a side of the examination opening, diametrically opposite the first height adjuster with respect to an aperture in the gantry. A patient on one height adjuster may be moved into the gantry while being additionally supported on the opposite side of the gantry on the opposite height adjuster.

BRIEF DESCRIPTION OF THE DRAWINGS

Exemplary embodiments of the invention are described in further detail below in conjunction with the drawings. Shown are.

DETAILED DESCRIPTION

Exemplary embodiments may be better understood with reference to the drawings, but these examples are not intended to be of a limiting nature. Like numbered elements in the same or different drawings perform equivalent functions.

Figure 1:
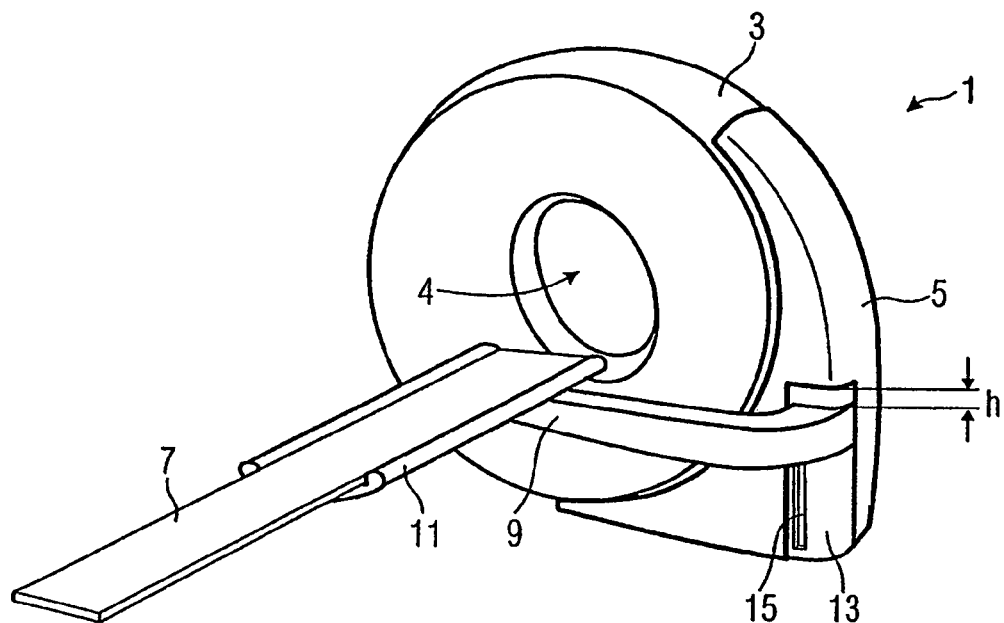
FIG. 1, a device for supporting a patient at a gantry.

FIG. 1 shows a device for supporting a patient at a computer tomography device (CT) 1. The CT 1 has a gantry 3, inside of which an X-ray beam source, and a diametrically opposed X-ray image detector rotate (the X-ray beam source and detector are not shown). The center of rotary motion is located in the examination opening 4 of the gantry 3. A patient to be examined is slid into the examination opening 4, and both the X-ray beam source and the X-ray image detector rotate around the patient and acquire the raw image data.

A device 5 for supporting a patient is mounted on the gantry 3 and is adapted to support a stretcher 7, on which a patient can be laid. The stretcher 7 is held by a stretcher guide 11 such that the stretcher 7 is longitudinally displaceable with respect to the stretcher guide 7. The range of longitudinal displacement may be such that the stretcher 7 is thrust out of the examination opening 4 so a patient can be placed on the stretcher 7. In that position, the stretcher 7 is readily accessible. The stretcher 7 is slid, with the patient, into the introduction opening 4 for the purpose of acquiring the raw CT image data.

The stretcher guide 11 is supported by a load-bearing arm 9, with which it is solidly connected. The load-bearing arm 9 is supported by a load-bearing arm bearing 13. The load-bearing arm bearing 13 is connected to a height adjuster 15, by which the height of the load-bearing arm 9 can be adjusted. In FIG. 1, the load-bearing arm 9 is not shown at a maximum height but instead has been slightly lowered by a distance h.

The amount of the lowering of the load-bearing arm 9 is limited only by the capability of the height adjuster 15. As such, load-bearing arm 9, and thus the stretcher 7, can be lowered as far as the height adjuster 15 permits, with a maximum lowering placing the stretcher onto or near the floor of the examination room where the CT 1 is located. Because of the lateral location of the height adjuster 15 with respect to the CT 1, the height adjuster 15 does not limit the maximum possible lowering, since it is not located between the stretcher 7 and the floor of the examination room. As a result, the stretcher 7 can be lowered optimally for each specific medical situation so that, for instance, a patient can be laid on the stretcher 7 with reduced effort. If needed, a patient can be placed on the stretcher 7 that has been lowered to near the floor, and the stretcher then raised to the level of the examination opening 4 so that the stretcher 7 can be introduced into the examination opening 4.

Figure 2:
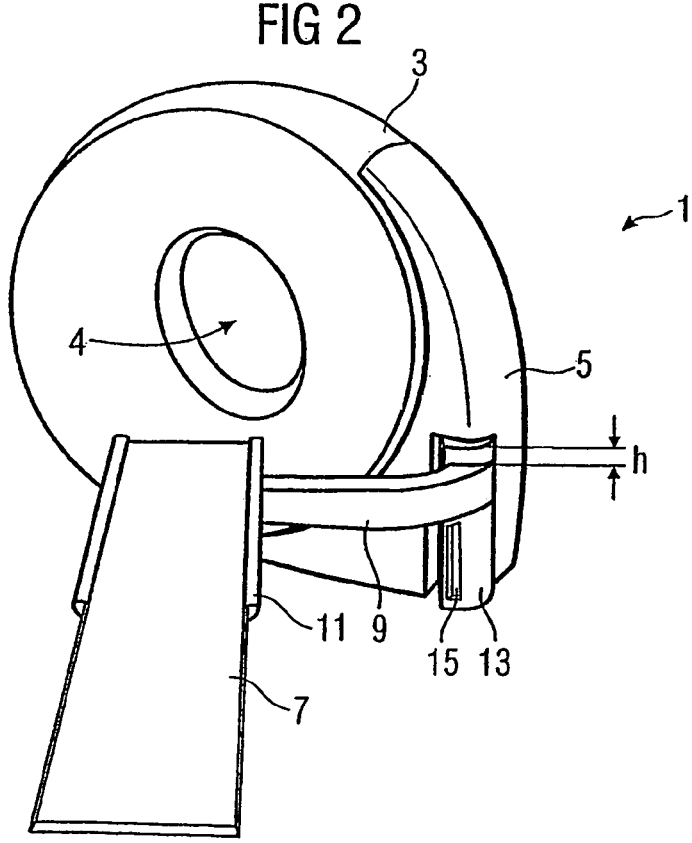
FIG. 2, the device for supporting a patient in a pivoted position.

In an aspect shown in FIG. 2, the load-bearing arm 9 that carries the stretcher 7 is supported in the device 5 for supporting a patient rotatably about a vertical axis. The load-bearing arm 9 is shown pivoted about the vertical axis of rotation such that the stretcher guide 11 and the stretcher 7 are rotated away from the gantry 3 The load-bearing arm 9 is pivoted together with the load-bearing arm bearing 13 and the height adjuster 15. Alternatively, the load-bearing arm 9 may be supported rotatably in the load-bearing arm bearing 13, so that only the load-bearing arm 9 is pivoted independently of the load-bearing arm bearing 13 and the height adjuster 15.

Figure 3:
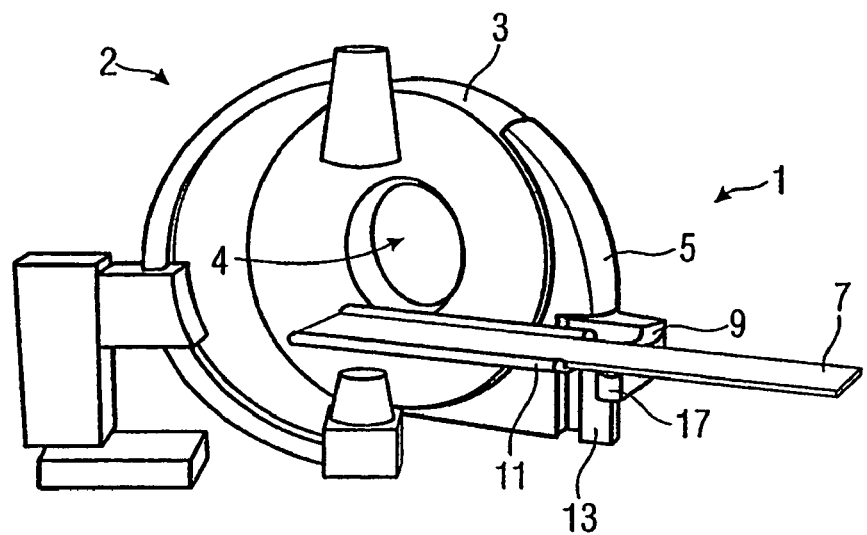
FIG. 3, the device for supporting a patient pivoted toward a C-arch X-ray machine.

In another aspect, FIG. 3 shows a C-arch X-ray machine 2 and a CT 1. The load-bearing arm 9, together with the stretcher 7, is shown pivoted away from the gantry 3 and into the vicinity of the C-arch X-ray machine 2. A patient lying on the stretcher 7 can be moved back and forth between the CT 1 and the C-arch X-ray machine 2 without having to be shifted from one stretcher to another. Instead, the patient can stay on the stretcher 7 and be moved back and forth by means of the pivoting motion of the device for supporting a patient.

A rotary bearing 17 supports the stretcher 7 rotatably about a vertical axis, and the rotary bearing 17 is mounted on the load-bearing arm 9. With the additional rotary motion, the exact positioning of the patient, either in the CT 1 or in the C-arch X-ray machine 2 is facilitated. The clear space required for the pivoting motion when pivoting the load-bearing arm 9 can also be optimized. In the rotary position shown for the stretcher 7, this radius is small, whereas the required clear space would be maximal with the stretcher 7 rotated by 90° with respect to the load-bearing arm 9. Varying the radius of the pivoting motion also expands the range for moving the patient from one device to another using the device for supporting a patient. As a result, the patient can be moved to other devices, not shown, without having to be shifted from one stretcher to another.

Figure 4:
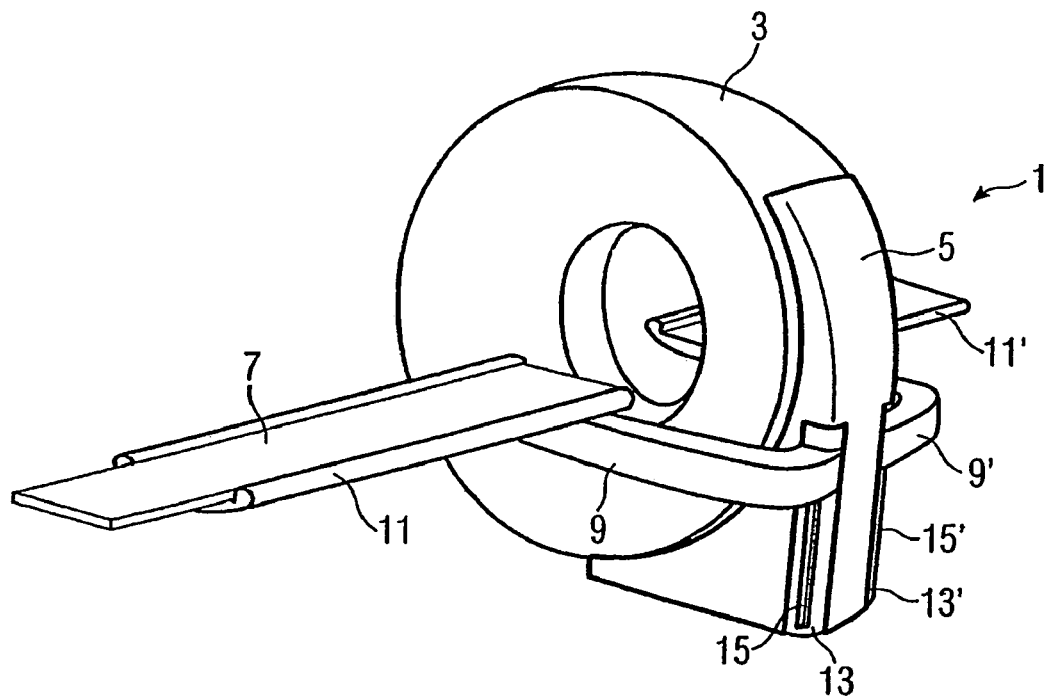
FIG. 4, a device for supporting a patient with a second height adjuster.

In yet another aspect shown in FIG. 4, CT 1 has a device 5 for supporting a patient with a load-bearing arm 9 and a stretcher guide 11 as previously described. A stretcher 7 rests on the stretcher guide 11. Laterally with respect to the gantry, there is a height adjuster 15, which supports the load-bearing arm 9 adjustably in height in the load-bearing arm bearing 13.

A further load-bearing arm 9' is provided, having a further stretcher guide 11'. The load-bearing arm 9' is supported in a load-bearing arm bearing 13' and is supported adjustably in height by a height adjuster 15'. The height adjuster 15', together with the load-bearing arm bearing 13' and the load-bearing arm 9', is located on the opposite side of the examination opening 4 with respect to the passage direction.

As a result of the lateral location of the height adjuster 15' next to the gantry 3 and thus next to the examination opening 4, the maximum lowerability of the stretcher guide 11' on the load-bearing arm 9' is possible. A patient lying on the stretcher 7 can be slid from the stretcher guide 11 into the examination opening 4 and advanced as far as stretcher guide 11'. Because of the support of the patient on the further stretcher guide 11', sagging of the stretcher 7 because of the patient's weight can be reduced. Once the raw CT image data has been acquired with the patient lying on the first stretcher guide 11, the patient on the stretcher 7 can be slid all the way through to the other side of the examination opening 4 with the stretcher 7 being supported by stretcher guides 11 and 11' as appropriate. When the stretcher is supported on stretcher guide 11', the patient can be moved for instance to a different medical device or taken to a place where another medical action is taken. For that purpose, the movement capabilities described in conjunction with the preceding examples can be performed by the load-bearing arm 9' and the stretcher guide 11'.

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. A device for supporting a patient with respect to a computer tomography device, the computer tomography device having a mounting surface, comprising:
    a gantry with an examination aperture operable to receive a patient to be examined;
    a height adjusting device mounted on the gantry; and
    a load-bearing support arm operable to support a stretcher and connected with the height adjusting device such that the load-bearing support arm is adjustable in height, and the load-bearing support arm is rotatable about an axis oriented vertical to the mounting surface of the computer tomography device when the gantry is positioned to receive a patient and the mounting surface rests on a floor.

2. The device of claim 1 further comprising:
    a stretcher guide, the stretcher guide operable to support the stretcher for longitudinal displacement.

3. The device of claim 1, further comprising
    a stretcher guide adapted to slidably receive the stretcher, the stretcher guide connected with the height adjusting device.

4. The device of claim 3, wherein the stretcher guide is adapted to permit a stretcher inserted therein to be displaced horizontally.

5. The device of claim 4, further comprising:
    a second height adjusting device mounted on the computer tomography device, a mounting axis of the second height adjusting device displaced laterally from an axis of symmetry of the examination aperture.

6. The device of claim 5 wherein the second height adjusting device is operable to support a stretcher adjustably in height.

7. The device of claim 5 further comprising:
    a second load-bearing support arm rotatable about the second height-adjusting device; and
    a second stretcher guide mounted to the second support arm.

8. The device of claim 7, wherein the stretcher guide and the second stretcher guide are disposed at opposite sides of the examination aperture.

9. A medical system, comprising:
    a computerized tomography device having an X-ray source and an X-ray detector disposed within a gantry having an aperture configured for accepting a patient along a gantry axis thereof; and
    a height adjusting device operable to support a stretcher, the height adjusting device mounted to the gantry and a mounting axis of the height adjusting device is displaced laterally from the gantry axis when the gantry is positioned to receive a patient.

10. The medical system of claim 9 further comprising:
    a load-bearing support arm rotatable about the height-adjusting device; and
    a stretcher guide mounted to the support arm.

11. The system of claim 9, further comprising:
    a second height adjusting device mounted to the gantry and a mounting axis of the second height adjusting device is displaced laterally from the gantry axis the aperture.

12. The system of claim 11 further comprising:
    a second load-bearing support arm rotatable about the second height-adjusting device; and
    a second stretcher guide mounted to the second load-bearing support arm.

13. The system of claim 12, further comprising
    a stretcher guide adapted to slidably receive the stretcher, the stretcher guide connected with the load-bearing support arm;
    wherein the stretcher guide and the second stretcher guide are adapted such that the stretcher may be transferred between the stretcher guide and the second stretcher guide while remaining in continuous contact with at least one of the stretcher guide and the second stretcher guide.

14. The system of claim 9, further comprising
    a stretcher guide adapted to slidably receive the stretcher, the stretcher guide connected with the height adjusting device.

* * * * *